(12) United States Patent
Kaestner

(10) Patent No.: US 10,105,388 B2
(45) Date of Patent: Oct. 23, 2018

(54) MEDICINAL CLAY PREPARATION

(71) Applicant: HEILERDE-GESELLSCHAFT LUVOS JUST GMBH & CO. KG, Friedrichsdorf (DE)

(72) Inventor: Ariane Kaestner, Friedrichsdorf (DE)

(73) Assignee: HEILERDE-GESELLSCHAFT LUVOS JUST GMBH & CO. KG, Friedrichsdorf (DE)

( * ) Notice: Subject to any disclaimer, the term of this patent is extended or adjusted under 35 U.S.C. 154(b) by 45 days.

(21) Appl. No.: 14/416,526

(22) PCT Filed: Jul. 26, 2013

(86) PCT No.: PCT/EP2013/002220
§ 371 (c)(1),
(2) Date: Apr. 16, 2015

(87) PCT Pub. No.: WO2014/015992
PCT Pub. Date: Jan. 30, 2014

(65) Prior Publication Data
US 2016/0101129 A1 Apr. 14, 2016

(30) Foreign Application Priority Data
Jul. 27, 2012 (DE) ........................ 10 2012 014 848

(51) Int. Cl.
*A61K 33/00* (2006.01)
*A61K 9/16* (2006.01)
*A61K 9/50* (2006.01)
*A61K 35/02* (2015.01)

(52) U.S. Cl.
CPC ............ *A61K 33/00* (2013.01); *A61K 9/1652* (2013.01); *A61K 9/5015* (2013.01); *A61K 9/5042* (2013.01); *A61K 35/02* (2013.01)

(58) Field of Classification Search
CPC ...... A61K 33/00; A61K 35/02; A61K 9/2054; A61K 33/12; A61K 33/06; C01P 2004/50
See application file for complete search history.

(56) References Cited

U.S. PATENT DOCUMENTS

| | | | | |
|---|---|---|---|---|
| 4,050,869 A * | 9/1977 | Takewell | ................... | B01J 2/12 264/117 |
| 5,061,397 A * | 10/1991 | Goodman | ............... | C11D 3/126 106/416 |
| 5,129,953 A * | 7/1992 | Suitch | .................... | D21H 17/68 106/416 |
| 5,196,473 A * | 3/1993 | Valenta | ................ | A01K 1/0154 252/383 |
| 5,206,010 A * | 4/1993 | Inoue | ..................... | A61Q 11/00 424/489 |
| 5,840,320 A * | 11/1998 | Odom | ....................... | A61K 8/26 424/401 |
| 2006/0204574 A1* | 9/2006 | Ogawa | .................... | A61K 9/282 424/468 |
| 2007/0014857 A1* | 1/2007 | Becourt | ............... | A61K 9/0095 424/464 |
| 2007/0077294 A1* | 4/2007 | Sherman | .............. | A61K 9/1641 424/451 |
| 2008/0038337 A1* | 2/2008 | Li | ......................... | A61K 9/2054 424/464 |
| 2008/0319476 A1* | 12/2008 | Ward | ................... | A61L 26/0004 606/213 |

FOREIGN PATENT DOCUMENTS

| | | | | |
|---|---|---|---|---|
| DE | 202008006245 U1 * | 8/2008 | ........... | A61K 9/0065 |
| DE | 10 2008 019339 A1 | 10/2009 | | |
| KR | 100984057 B1 * | 9/2010 | | |

OTHER PUBLICATIONS

Williams et al., Int. Geol. Rev, 52: 745-770 (2011).*
More about Heilerde, Luvos Helerde, English language translation accessed via the Internet Archive Wayback Machine, captured 2007.*
"Mineral Content of Luvos Healing Earth", DIMEX (2009).*
AkzoNoble, https://www.akzonobel.com/colloidalsilica/function/binding/, downloaded May 25, 2016.*
Ashland, Pharmaceutical Technology Report, PRT-095 (2014).*
Scholz, Textatelier, May 31, 2010, accessed at http://webcache.googleusercontent.com/search?q=cache:YvTF3xhGpJIJ:www.textatelier.com/index.php%3Fid%3D996%26blognr%3D3366+&cd=10&hl=en&ct=clnk&gl=us, with citations referring to Google translation attached.*
"Clastic Sedimentary Rock Classification", accessed at http://csmres.jmu.edu/geollab/Fichter/SedRx/ Clastic.html May 24, 2016.*
Dias et al., COLORCON (2008).*
Determination of Ethylcellulose as Being Generally Recognized as Safe, DOW Chemical (2013).*
Galan, Clay Minerals, 31: 443-453 (1996).*
Viseras et al., Applied Clay Science, 36: 37-50 (2007).*
Park et al., EPO translation of KR 100984057, accessed at http://translationportal.epo.org/emtp/translate/?ACTION=description-retrieval&COUNTRY=KR&ENGINE=google&FORMAT=docdb&KIND=B1&LOCALE=en_EP&NUMBER=100984057&OPS=ops.epo.org/3.2&SRCLANG=ko&TRGLANG=en on Aug. 16, 2017.*
EPO machine translation of DE 202008006245U1, downloaded Feb. 22, 2018 (Year: 2008).*
Sigma-Aldrich, Particle Size Conversion Table (downloaded from https://www.sigmaaldrich.com/chemistry/stockroom-reagents/learning-center/technical-library/particle-size-conversion.printerview.html, Feb. 27, 2018 (Year: 2004).*

(Continued)

Primary Examiner — Bethany P Barham
Assistant Examiner — Barbara S Frazier
(74) Attorney, Agent, or Firm — Dickinson Wright PLLC

(57) ABSTRACT

The present invention relates to a medicinal clay preparation containing 90-99.9% w/w medicinal clay and 0.1-10% w/w binders. It further relates to a method for producing the medicinal clay preparation, wherein first the binder(s) is/are dissolved or suspended in purified water and then the medicinal clay is mixed with the binder-water mixture and granulated by a conventional method. Optionally, a coating can also be subsequently applied.

9 Claims, No Drawings

(56) References Cited

OTHER PUBLICATIONS

Uehleke B: Luvos-Heilerde—ein Bewährtes Naturheilmittel im Blick Neuer Forschung, Internet Citation, Oct. 2005, pp. 1-4, XP002541877, Retrieved from the Internet: URL:http: //www.luvos.de/data/luvos/media/doc/Naturehilkunde_Journal_10_2005.pdf.
Jaminet F: Research on the Action of Adjuvants of Tablets on Certain Characteristics of the Latter. I. Influence of the Viscosity of Sodium Carboxymethylcellusoses Used as Binders and as Disintegrators on the Speed of Disintegration of Kaolin Tablets, Journal de Pharmacie de Belgique, Masson, Paris, Fr., vol. 19, Mar. 1, 1964, pp. 144-150, XP009122030, ISSN: 0047-2166, p. 147; examples 1-9.

* cited by examiner

MEDICINAL CLAY PREPARATION

The present invention relates to a medicinal clay preparation including excipients. This preparation contains at least one binder and, optionally one coating agent (coating). In addition, the present invention relates to a method for producing the medicinal clay preparation. The medicinal clay preparation has improved properties and may, for example, be applied internally.

Medicinal clay is obtained from ice age loess deposits and is a known and proven natural remedy.

In natural medicine, medicinal clay or loess is used for both internal and external application. The reasons for this are the small granular size, the high specific surface and the associated high adsorption and absorption capacity. Medicinal clay also exhibits a high acid binding capacity.

Thus, for internal application, for example, it is recommended in cases of heart burn, and acid-related stomach disorders to swallow small amounts of medicinal clay or loess elutriated in water. In such cases the medicinal clay is said to bind the excess stomach acid and bile acids. This is said to alleviate stomach disorders and to further protect the mucous membrane of the stomach from aggressive substances.

Diarrheal diseases may also be treated with an internal application of medicinal clay.

In addition, the substances and microorganisms harmful to the intestines may also be bound through the internal application of medicinal clay, which contributes to a general cleansing of the intestines. An intestinal cleansing of this kind is possible, both as it relates to disease and prophylactically. In the process, the medicinal clay binds various by-products of proteins derived from dietary protein such as, for example, skatole. Metabolic products excreted by intestinal bacteria, which in some cases harm the physiological intestinal flora, may also be absorbed or adsorbed by medicinal clay.

When applied externally, medicinal clay relieves acne, inflammations, disorders of the skin, muscles and joints. Medicinal clay is also used cosmetically for skin and beauty treatment, because it is said to lend the skin a fresh and attractive appearance. The result of the high adsorption and absorption capacity of medicinal clay is a cleansing of the skin, which eliminates the bases for acne and blemished skin.

For external applications, medicinal clay is normally mixed with water, then applied, for example, as a wrap, coating, bath or face mask.

For internal applications, medicinal clay may be stirred in water or tea and ingested.

The raw material for medicinal clay is loess. Once mined, it is dried, ground and sieved. The resultant medicinal clay is a very fine powder. Due to its physical nature, among other things, its large surface area, which, in addition to the material and chemical composition of medicinal clay, is partially responsible for the desired and advantageous effects, it is technically difficult to further process the finely ground power into other solid dosage forms. As a result, pure medicinal clay is usually offered in powder form.

Only in exceptional cases is the loess offered unground in rough chunks or as roughly broken granulate of lesser quality, as it exists following the mining and extraction process. The clay in this form, however, is a non-standardized product with variable properties.

An important process step is the drying, to allow the clay to become free-flowing and to be further processed. During this process step, a reduction in granular size also occurs, so that the clay becomes durable and the required maximum number of grains is never exceeded. A raw, unprocessed clay in which aggregates (chunks of medicinal clay) are still present should not be passed on to the end user. Without exception, high-quality medicinal clay is offered in powder form or as capsules or tablets In the case of internal application, users, when ingesting medicinal clay, notice in part that the swallowing of the medicinal clay is not ideal, since a fine medicinal clay powder remains behind in the mouth, and a "sandy" feel and a crunching is noticeable.

This is also impossible to completely eliminate, if, as is normally recommended, medicinal clay is elutriated in water or in a liquid and then imbibed.

An aqueous medicinal clay suspension, on the other hand, is visually relatively unappealing. The "muddy impression" of the powder stirred in water results in a negative mindset of the user due to the attitude of some that one does not take clay orally or eat it.

Moreover, medicinal clay settles out in water relatively quickly, which results in a negative taste experience for the last liquid residue, since the dregs contain more medicinal clay mixed with less water.

The medicinal clay when mixed in water also crunches in the mouth. That, too, contributes to a psychological barrier many humans have when ingesting medicinal clay.

In order to avoid the ingestion of medicinal clay mixed in water with the disadvantages described, medicinal clay is offered in the form of swallowable hard gelatin capsules. There are some people, however, who do not like to ingest or are unable to swallow capsules.

Given the orientation and intention of natural medicine of using preferably natural and pure substances, the medicinal clay should, if possible, be admixed with no other substances or with as few additional substances as possible. Furthermore, these additives themselves should be as natural as possible, pure or physiological, because this best allows the unadulterated effect of the medicinal clay itself to occur.

A composition for the prophylactic and/or curative treatment of hyperacidity is described in DE 10 2008 019 339 A1, in particular, in the form of an antacid, which contains medicinal clay, alginic acid and an acid-induced gas-releasing component. The composition may exist in liquid or solid form, as a suspension, powder, granulate or tablets. The medicinal clay in this case is included in an amount of 5 to 80% by weight, and preferably in an amount of 20 to 30% by weight.

Because of the ingredients of this composition which includes only a relatively small proportion of medicinal clay, the mixture described may be easily formed into granulate or tablets. However, for the aforementioned application in the sense of a natural product, such a combination of three different substances, namely medicinal clay, alginic acid/alginates and gas-releasing components is undesirable, since the medicinal clay as a natural product should be used as unadulterated as possible.

However, to date, medicinal clay in virtually pure form has been almost impossible to produce, since the abrasive nature of the powder causes severe abrasion of the tools.

The object of the present invention, therefore, is to provide a medicinal clay in a preparation, which facilitates application and which does not exhibit the aforementioned disadvantages. At the same time, a medicinal clay preparation is intended to be found, which, in particular for internal application, is mixed with as few additives possible.

The object of the present invention is also to provide a method, with which the described medicinal clay preparation according to the present invention may be produced.

The applicant unexpectedly found that this object may be achieved by a medicinal clay preparation, which contains 90-99% by weight of medicinal clay and 0.1-10% by weight of binder. Preferably, the medicinal clay preparation contains 0.5 to 5.0% by weight of binder, and particularly preferably 0.5 to 2.0% by weight of binder.

The term "medicinal clay" within the meaning of the present invention comprises an earthen clay mineral extracted from loess deposits. Loess is a sediment classified as a clastic rock and, in this case, as a siltstone. It consists of uniform, extremely fine quartz dust interfused with 8-20% limestone fragments, together with a clayey binder tinted yellow by iron hydroxides. The proportion of clay is 5-15%, the proportion of fine sand (clastic rock) is 10-20%.

Mineralogically, medicinal clay is made up essentially of silicates (more than 50%), three-layer clay minerals, feldspar, calcite and dolomite. In terms of elements, it contains mainly oxygen, silicon, calcium, aluminum, iron and potassium; additionally, proportions of less than 1% of magnesium, sodium, titanium and phosphorous.

The composition and the color of medicinal clay may vary, due to the fact that it is a natural product, and due to the natural conditions of the mining sites.

Medicinal clay is a very fine-grained powder. The maximum particle size distribution varies between 20 and 50 µm.

The expression "contains" or "contain" within the meaning of the present invention does not describe an exhaustive listing.

Furthermore, the term "internal application" within the meaning of the present application relates to an application in the gastro-intestinal tract and in the mouth. An external application within the meaning of this invention is understood to mean the application to the skin, scalp and hair.

For the present invention, the term "extrudate" is used largely synonymously with the term "granulate". The object of the present invention is to make a dosage form based on the long-existing medicinal clay powder, which is easier to administer, easily measured into doses and ingested. This dosage form represents a medicinal clay preparation which has been agglomerated into relatively large particles with the aid of a binder. These particles adhered together by means of the binder are referred to as granulate. The granulate described herein may also be referred to as extrudate, based on the aforementioned manufacturing process (extrusion).

According to another aspect of the invention, the medicinal clay preparation containing medicinal clay and binder may be layered with a coating in an amount of 0.1-10% by weight, relative to the total weight of the preparation.

A content of 0.5 to 5.0% by weight of coating is preferred, and particularly preferably a content of 1.5 to 5.0% by weight of coating, relative to the total weight of the preparation.

The preparation exists preferably as a non-coated or as coated granulate having an average particle diameter of approximately 1.5 to 2.5 mm. An average particle diameter of approximately 1.8 to 2.2 mm would be particularly suitable. The medicinal clay in granulate form has many advantages as compared to the previously known medicinal clay in powder form.

The medicinal clay preparation according to the invention, in particular in the form of granulate, makes it easy for the user to comfortably ingest. Thus, the granulate may be placed directly in the mouth using a spoon. The preparation is easy to swallow, either by swallowing the granulate already in the mouth with water, or by swallowing it directly. In the process, the granulate does not adhere to the oral mucosa. Moreover, the preparation does not crunch when ingested, and surprisingly is tasteless in spite of the merely minimal addition of binder and, optionally, of the coating layer. Coated granulate according to claim 2 is even easier to swallow, in particular, if one wishes to swallow without additional liquid.

Because of the binder in the concentration according to the invention, the medicinal clay preparation, once ingested, maintains its form for a sufficient period of time, so that it survives the passage through the mouth in its original form and dissolves in the stomach only after being swallowed.

It was unexpected that such a stable granulate can be obtained with a small amount of binder of only 0.1 to 10% by weight. On the one hand, the granulate, in spite of the small binder fraction, remains stable during a potential further treatment or further processing such as, for example, a drying or coating in the fluidized bed. A granulate with low stability in this case would result in an undesirably high loss due to finely abraded fractions. It may also be easily transported and/or finished without a breakdown of the agglomerates having to be anticipated. On the other hand, it does not disintegrate prematurely in the mouth when ingested, which is important in terms of pleasant ingestion on the part of the user. Only if the granulate remains stable until after swallowing, is possible to avoid the earthy taste, which arises when ingesting the medicinal clay powder.

Moreover, the granulate is easier to handle due to the improved free-flowing dosage form, for example, when pouring it out from a storage vessel. A uniform dosing is also easier in the case of a product which is easily poured.

According to another embodiment, the granulate is filled in portions and in this way may be taken orally directly from the packaging. Even in the process of proportional filling, the medicinal clay in granulate form has advantages over the powder form.

With respect to the medicinal clay preparation according to the invention, the binder contained therein may include one or more water soluble polymers. In this case, polymers are preferred, which are inert to the extent possible and/or consist of natural substances, and are therefore in accord with the principles of natural remedies. Conceivable binders would be, for example, starches, tragacanth or cellulose ether.

Cellulose acetate, ethyl cellulose, methyl cellulose, hydroxypropyl cellulose, hydroxypropyl methyl cellulose, carboxymethyl cellulose and polyvinyl alcohol are particularly suitable.

Primarily, the cellulose ethers, such as methyl cellulose or hydroxypropyl methyl cellulose are suitable. The base structure of the cellulose ethers, the backbone, is cellulose, a naturally occurring polymer. Partial replacement of the hydroxyl groups, best adapts hydrophilia or hydrophobia to the requirements. The degree of substitution of methyl cellulose may preferably be 1.3 to 2.6, in particular, 1.6 to 2.0; a preferred degree of polymerization is approximately 50 to 1,000. This corresponds to an average molar mass of the methyl polymers of approximately 10,000 to 220,000 g/mol.

The cellulose ethers, since they are not degraded in the intestine, are soluble in cold water and also do not react with the components of the medicinal clay, are well suited for combining with this natural product.

The coating that may be used to layer the medicinal clay preparation according to the invention may contain one or more water-soluble polymers or film formers. Here, too, it should be noted that the film former is inert to the extent possible and cannot undergo any undesired reactions with the medicinal clay. Moreover, the unique effect of the film former should not influence the effect of the medicinal clay in the body. In this case, starches, modified starches, maltodextrins, sucrose, cellulose ethers, cellulose acetate are suitable.

These film formers may be selected, in particular, from cellulose acetate, ethyl cellulose, methyl cellulose, hydroxypropyl methyl cellulose, polyvinyl alcohol, maltodextrin and gum Arabic. Mixtures of two or more of the aforementioned film formers are also possible.

Modified starches (for example, INSTANT PURE-COTE® B793, PURE-DENT® B815) or maltodextrins (such as Maltrin M040, Maltrin® M150, Maltrin® M100) are particularly preferred.

The medicinal clay used according to the invention is distinguished by the fact that it is extracted from loess, an ice age sediment. The medicinal clay contains quartz dust, which is interfused with 8-20% limestone fragments. It also contains a proportion of 10 to 20% by weight of fine sand consisting of clastic rock, and of 5 to 15% by weight of clay mineral, which is tinted yellow by iron hydroxide. The color varies depending on the composition, as is typical of a natural product. The proportion of quartz dust with limestone fragments is highest at 65 to 85% by weight.

The medicinal clay used according to the invention may, for example, contain silicates of aluminum, magnesium and calcium, as well as mixtures of these silicates, in addition to three layer clay minerals, in particular illite, smectite and/or colorit, feldspars, calcite and dolomite.

The aforementioned components of the medicinal clay include at least one element from the group of silicon, oxygen, calcium, aluminum, iron, potassium, magnesium, sodium, titanium and phosphorous, preferably bonded as silicates, hydroxides or carbonates.

In addition, the medicinal clay used according to the invention may contain trace elements such as, for example, copper, manganese, nickel, selenium and zinc.

The bulk density of the medicinal clay preparation according to the invention may be in the range of 880 to 980 g/l. Preferably, it is 920 to 940 g/l. Thus, it is below the bulk density of pure medicinal clay.

The administration in the form of granulate is suitable for enabling larger single doses than is the case with capsules.

The filling of the medicinal clay preparation according to the invention—for example, as granulate—may occur as bulk material in the form of 100 to 500 g bunches. Preferable is a filing in sachets, however. In this case, sachets having a single dose of approximately 6-7 g are particularly preferable.

The medicinal clay preparation according to the invention may be produced according to a method, in which in a first step (a) the binder is dissolved in purified water. The binder is advantageously dissolved in cold purified water. In a second subsequent step (b), the medicinal clay is added to the binder solution (a) and mixed. In this way, the medicinal clay is moistened. Subsequently, the moist mass is pressed with the aid of a common extruder under pressure through openings of a specific size.

In this case, a perforated facia extruder, single-screw extruder or double-screw extruder may be used.

The medicinal clay may be mixed or moistened with the binder solution, depending on the type of extruder used, as described above, before entering the extruder or, alternatively, in the extruder itself.

In the case in which the medicinal clay is first added to the binder solution in the extruder, a mixing or moistening step preceding extrusion is unnecessary. Hence, this method, in which the medicinal clay is moistened in the extruder itself, is particularly advantageous, since it is less complex and therefore also more cost-efficient.

In another implementation of the method according to the invention, the medicinal clay granulate obtained from the extrusion is dried in a fluidized bed.

The granulate may then be optionally layered with a coating in a step (c) according to a conventional method.

This coating occurs particularly preferably in an operational step immediately following drying in the same fluidized bed or it is dried and coated simultaneously.

Both the drying and the optional coating according to (c) may be continued until the desired final moistness is achieved and the coating is applied in the desired thickness.

An extrudate of sufficient stability is obtained, in spite of the low binder content of 0.1 to 10% by weight.

The present invention is explained with reference to the following exemplary embodiments, which serve merely to illustrate without limiting the invention to the scope of these examples:

Preparation 1 (According to the Invention)

A preparation according to the invention in the form of a granulate is prepared from the following ingredients:

| Ingredients | Amount in kg per charge | Amount in % by weight in the final product |
| --- | --- | --- |
| Medicinal clay | 400.0 | 99.09 |
| Methyl cellulose | 3.68 | 0.91 |
| Water (purified) | q.s. | |

The required amount of methyl cellulose is dissolved in a specific amount of cold water.

For the purpose of granulation, the loess is moistened with a methyl cellulose solution and bonded. Once the entire binder solution provided is introduced, the loess thus moistened is conveyed to the entry of the single-screw extruder. For this purpose, a silicone tube is used, by way of which the moist mixture passes directly into the material inlet of the extruder. Extrusion takes place through a 2.0 mm matrix.

Subsequent to extrusion, the still moist granulate is dried in a fluidized bed facility. During the drying step, the product is heated to a moderate 25 to 35° C.

Preparation 2 (According to the Invention)

| Ingredients | Amount in kg per charge | Amount in % by weight in the final product |
| --- | --- | --- |
| Medicinal clay-methyl cellulose-granulate | 390.60 | 97.65 |
| Methyl cellulose | 6.28 | 1.57 |
| Maltodextrin | 3.12 | 0.78 |
| Water (purified) | q.s. | |

Maltodextrin and methyl cellulose are loosely mixed and dissolved in the required amount of cold purified water.

The extrudate obtained as preparation 1 is sprayed gradually with the methyl cellulose-maltodextrin solution in the fluidized bed facility, until the entire amount of coating solution (coating) is applied. Subsequently, the fluidized bed is further operated at a similar temperature until the coating is also dried.

After applying the required amount of coating, and without exceeding the maximum residual moisture, the granulate is cooled. The finished product is removed from the fluidized bed and subjected to a protective sieving. In the process, both oversized grains (>2.5 mm) as well as undersized grains (<1 mm) are separated out.

For intermediate storage and further transport, the finished intermediate product is poured into PE bags in 20 kg bunches and tightly sealed.

Preparation 3 (According to the Invention)

| Ingredients | Amount in kg per charge | Amount in % by weight in the final product |
| --- | --- | --- |
| Medicinal clay | 392.20 | 98.05 |
| Ethyl cellulose | 4.20 | 1.05 |
| Methyl cellulose | 3.60 | 0.90 |
| Water (purified) | q.s. | |

The required amount of ethyl cellulose and methyl cellulose are loosely mixed and dissolved in a sufficient amount of cold water.

For the purpose of granulation in the double-screw extruder, the medicinal clay is delivered directly to the intake zone of the extruder. In the compaction zone of the extruder, the medicinal clay is moistened during compaction with the ethyl cellulose-methyl cellulose solution. A step preceding granulation for mixing medicinal clay and binder solution is unnecessary. Extrusion takes place through a 2.0 mm matrix.

Subsequent to extrusion, the still moist granulate is dried in a fluidized bed facility. During the drying step, the product is heated to a moderate 25 to 35° C.

Preparation 4 (According to the Invention)

The granulate obtained under 3 is coated with the following additives:

| Ingredients | Amount in kg per charge | Amount in % by weight in the final product |
| --- | --- | --- |
| Medicinal clay-ethyl cellulose-methyl cellulose-granulate | 387.0 | 96.75 |
| Ethyl cellulose | 10.0 | 2.50 |
| Methyl cellulose | 1.6 | 0.40 |
| Maltodextrin | 1.6 | 0.40 |
| Water | q.s. | |

Ethyl cellulose, methyl cellulose and maltodextrin are loosely mixed and dissolved in the requirement amount of cold purified water.

The extrudate obtained as preparation 3 is sprayed gradually with the ethyl cellulose-methyl cellulose-maltodextrin solution in the fluidized bed facility, until the entire amount of coating solution (coating) is applied. Subsequently, the fluidized bed is further operated at a similar temperature until the coating is also dried.

After applying the required amount of coating, and without exceeding the maximum residual moisture, the granulate is cooled. The finished product is removed from the fluidized bed and subjected to a protective sieving. In the process, both oversized grains (>2.5 mm) as well as undersized grains (<1 mm) are separated out.

For intermediate storage and further transport, the finished intermediate product is poured into PE bags in 20 kg bunches and tightly sealed.

Preparation 5 (According to the Invention)

A preparation according to the invention in the form of a granulate is prepared from the following ingredients:

| Ingredients | Amount in kg per charge | Amount in % by weight in the final product |
| --- | --- | --- |
| Medicinal clay | 396.0 | 99.0 |
| Hydroxypropyl-methyl cellulose | 4.0 | 1.0 |
| Water (purified) | q.s. | |

The required amount of hydroxypropyl methyl cellulose is dissolved in a sufficient amount of cold water.

For the purpose of granulation in the double-screw extruder, the medicinal clay is delivered directly to the intake zone of the extruder. In the compaction zone of the extruder, the medicinal clay is moistened during compaction with the hydroxypropyl methyl cellulose solution. A step preceding granulation for mixing medicinal clay and binder solution is unnecessary. Extrusion takes place through a 2.0 mm matrix.

Subsequent to extrusion, the still moist granulate is dried in a fluidized bed facility. During the drying step, the product is heated to a moderate 25 to 35° C.

Preparation 6 (According to the Invention)

The granulate obtained under 5 is coated with the following additives:

| Ingredients | Amount in kg per charge | Amount in % by weight in the final product |
| --- | --- | --- |
| Medicinal clay-HPMC-granulate | 389.8 | 97.45 |
| Hydroxypropyl-methyl cellulose | 6.72 | 1.67 |
| Maltodextrin | 3.56 | 0.88 |
| Water | q.s. | |

Hydroxypropyl methyl cellulose and maltodextrin are loosely mixed and dissolved in the requirement amount of cold purified water.

The extrudate obtained as preparation 5 is sprayed gradually with the hydroxypropyl-methyl cellulose-maltodextrin solution in the fluidized bed facility, until the entire amount of coating solution (coating) is applied. Subsequently, the fluidized bed is further operated at a similar temperature until the coating is also dried.

After applying the required amount of coating, and without exceeding the maximum residual moisture, the granulate is cooled. The finished product is removed from the fluidized bed and subjected to a protective sieving. In the process, both oversized grains (>2.5 mm) as well as undersized grains (<1 mm) are separated out.

For intermediate storage and further transport, the finished intermediate product is poured into PE bags in 20 kg bunches and tightly sealed.

Preparation 7 (According to the Invention)

A preparation according to the invention in the form of a granulate is prepared from the following ingredients:

| Ingredients | Amount in kg per charge | Amount in % by weight in the final product |
|---|---|---|
| Medicinal clay | 399.84 | 99.96 |
| Ethyl cellulose | 0.12 | 0.03 |
| Methyl cellulose | 0.04 | 0.01 |
| Water (purified) | q.s. | |

Ethyl cellulose and methyl cellulose are loosely mixed and dissolved in the required amount of cold purified water.

The medicinal clay moistened with the binder solution is introduced into a single-screw extruder. The extruded mass already disintegrates in part upon introduction into the fluidized bed. After a brief period in the fluidized bed no useable agglomerates remain.

This shows that the amounts of medicinal clay and binder used in the present invention are selected so that a stable granulate is obtained even with a relatively small amount of binder.

The granulate according to the invention has the described advantages as compared to the previously used medicinal clay powder without the need for using an unnecessarily high amount of excipients.

The invention claimed is:

1. A medicinal clay preparation, comprising granules consisting essentially of 90-99.9% by weight of medicinal clay and 0.1-10% by weight of a water soluble binder, said granules having a coating in an amount of 1.5%-5.0% by weight relative to the total weight of the coated granules, wherein the medicinal clay comprises earthen clay mineral extracted from loess deposits, wherein said earthen clay comprises quartz dust interfused with 8-20% by weight limestone fragments and 5 to 15% by weight clay, and where said coating contains one or more water soluble polymers or water soluble film formers selected from the group consisting of starches, modified starches, sucrose, cellulose acetate, methyl cellulose, hydroxypropyl methyl cellulose, polyvinyl alcohol, maltodextrin, and gum Arabic, and said coated granules having an average particle size of about 1.5 to 2.5 mm.

2. The medicinal clay preparation according to claim 1, containing 95-99.5% by weight of medicinal clay and 0.5-5.0% by weight of the granules binder relative to the total weight of the granules.

3. The medicinal clay preparation according to claim 1, containing 98-99.5% by weight of medicinal clay and 0.5-2.0% by weight of binder relative to the total weight of the granules.

4. The medicinal clay preparation according to claim 1, wherein said water-soluble binder is selected from the group consisting of starches, tragacanth, cellulose acetate, cellulose ether, methyl cellulose, hydroxypropyl cellulose, hydroxypropyl methyl cellulose, carboxymethyl cellulose and polyvinyl alcohol.

5. The medicinal clay preparation according to claim 1, wherein the medicinal clay contains one or more components from the group of silicates of aluminum, magnesium and potassium, as well as mixtures of these silicates, three layer clay minerals, illite, smectite, feldspars, calcite and dolomite.

6. The medicinal clay preparation according to claim 1, wherein the medicinal clay contains at least one element from the group of silicon, oxygen, calcium, aluminum, iron, potassium, magnesium, sodium, titanium and phosphorous.

7. The medicinal clay preparation according to claim 6, wherein at least one of the elements copper, manganese, nickel, selenium and/or zinc is included as a trace element in the medicinal clay.

8. The medicinal clay preparation according to claim 1, wherein the preparation has a bulk density of 880 to 980 g/l.

9. A medicinal clay preparation unit package comprising sachets, each containing 6-7 g of the coated medicinal clay preparation of claim 1.

* * * * *